(12) United States Patent
Beals et al.

(10) Patent No.: US 7,723,291 B2
(45) Date of Patent: *May 25, 2010

(54) RELEASE OF BMP, BIOACTIVE AGENTS AND/OR CELLS VIA A PUMP INTO A CARRIER MATRIX

(75) Inventors: Neil Beals, Memphis, TN (US); Jeffrey L. Scifert, Arlington, TN (US); Vanja M. King, Memphis, TN (US)

(73) Assignee: Warsaw Orthopedic, Inc.

( * ) Notice: Subject to any disclaimer, the term of this patent is extended or adjusted under 35 U.S.C. 154(b) by 168 days.

This patent is subject to a terminal disclaimer.

(21) Appl. No.: 11/494,237

(22) Filed: Jul. 27, 2006

(65) Prior Publication Data
US 2008/0025987 A1 Jan. 31, 2008

(51) Int. Cl.
*A61K 38/16* (2006.01)
*A61K 38/17* (2006.01)
*A61K 38/18* (2006.01)
*A61K 38/22* (2006.01)
*A61K 38/30* (2006.01)
*A61M 31/00* (2006.01)
*A61M 1/00* (2006.01)

(52) U.S. Cl. .................. 514/2; 604/67; 604/151; 604/286; 514/801; 530/356

(58) Field of Classification Search .............. None
See application file for complete search history.

(56) References Cited

U.S. PATENT DOCUMENTS

| | | | |
|---|---|---|---|
| 5,354,557 A | 10/1994 | Oppermann et al. | |
| 5,958,441 A | 9/1999 | Oppermann et al. | |
| 6,551,995 B1 | 4/2003 | Oppermann et al. | |
| 6,586,388 B2 | 7/2003 | Oppermann et al. | |
| 6,919,308 B2 | 7/2005 | Oppermann et al. | |
| 6,949,251 B2 | 9/2005 | Dalal et al. | |
| 2003/0049328 A1 | 3/2003 | Dalal et al. | |
| 2003/0069401 A1 | 4/2003 | Oppermann et al. | |
| 2003/0180376 A1 | 9/2003 | Dalal et al. | |
| 2003/0224996 A1 | 12/2003 | Opperman et al. | |
| 2005/0112091 A1* | 5/2005 | DiMauro et al. | 424/85.1 |
| 2005/0169965 A1 | 8/2005 | Paulista et al. | |
| 2005/0170012 A1 | 8/2005 | Dalal et al. | |
| 2005/0255141 A1 | 11/2005 | Oppermann et al. | |
| 2007/0016163 A1* | 1/2007 | Santini et al. | 604/500 |

FOREIGN PATENT DOCUMENTS

WO  WO 91/11148  8/1991

\* cited by examiner

*Primary Examiner*—Elizabeth C. Kemmerer

(57) ABSTRACT

A pump to deliver bone-growth factors to a carrier matrix within a patient. Pump can be internal or external. With external pumps, additional amounts of the same growth factor may be added, or the bioactive agent may be changed during the course of treatment. An external pump permits the use of cells to promote bone growth. The pump can have several reservoirs and the pump can itself be received in the carrier matrix with an outlet tube or other structure to defuse the growth factors into the carrier matrix. The pump protocol can be used for slow-to-heal fractures, such as closed fractures, and can be used for slow-to-heal patients.

15 Claims, 8 Drawing Sheets

RELEASE OF BMP, BIOACTIVE AGENTS AND/OR CELLS VIA A PUMP INTO A CARRIER MATRIX

FIELD OF THE INVENTION

The present invention relates to methods and associated systems and kits for promoting bone growth at a site in a patient, and more specifically discloses utilizing a pump to supply a carrier matrix at the site with one or more therapeutic agents selected to promote bone growth.

BACKGROUND OF THE INVENTION

The use of bone morphogenetic proteins (BMPs) or other osteoinductive factors in combination with a suitable carrier matrix to promote bone growth and healing at a site in a patient is well known. Reference may be drawn, for example, to U.S. Pat. No. 6,551,995 to Oppermann et al., which is incorporated herein by reference, and to U.S. Pat. No. 6,949,251 to Dalal et al., also incorporated herein by reference.

Briefly, a highly porous, biodegradable carrier matrix is provided, which serves as a scaffolding for the formation of host bone tissue. This matrix is ideally impregnated with one or more osteoinductive factors and/or other bioactive agents. These bioactive agents may include, but are not limited to, antimicrobials, antibiotics, antimyobacterial, antifungals, antivirals, antineoplastic agents, antitumor agents, agents affecting the immune response, blood calcium regulators, agents useful in glucose regulation, anticoagulants, antithrombotics, antihyperlipidemic agents, cardiac drugs, thyromimetic and antithyroid drugs, adrenergics, antihypertensive agents, cholnergics, anticholinergics, antispasmodics, antiulcer agents, skeletal and smooth muscle relaxants, prostaglandins, general inhibitors of the allergic response, antihistamines, local anesthetics, analgesics, narcotic antagonists, antitussives, sedative-hypnotic agents, anticonvulsants, antipsychotics, anti-anxiety agents, antidepressant agents, anorexigenics, non-steroidal anti-inflammatory agents, steroidal anti-inflammatory agents, antioxidants, vaso-active agents, bone-active agents, osteogenic factors, osteoinductive factors, antiarthritics, and diagnostic agents. A preferred embodiment would include recombinant human BMPs (rhBMPs). The biodegradable matrix is then surgically placed at a target site where bone formation is desired, such as a fracture site or a spinal fusion site. The osteoinductive factors act much like a catalyst, encouraging the necessary cells (including, but not limited to, mesenchymal stem cells, osteoblasts, and osteoclasts) to more rapidly migrate into the matrix, which is eventually resorbed via a cell-mediated process and newly formed bone is deposited at the target site. In this manner severe fractures may be healed, and vertebrae successfully fused.

A singular problem is that the osteoinductive factors are often proteins, and hence subject to degradation from acids, enzymes and other compounds that leach both from tissue surrounding the target site and from the bone tissue growing into the carrier matrix. As a result, it is believed that the therapeutic efficacy of the carrier matrix and factors diminishes with time, and also as it is replaced with host tissue and as the osteoinductive factors leach from the carrier matrix. Although this may not be a problem for target sites where relatively fast bone growth is expected, this can become a problem when the bone growth is slow; such slow growth may be exhibited, for example, in closed fractures, and with patients with known co-morbidities, such as smokers, diabetics, and those on steroids.

It is therefore desirable to provide methods and related systems that insure that carrier matrices retain their full efficacy over time to maximally promote bone growth at a target site.

SUMMARY OF THE INVENTION

The present invention fills the foregoing need by providing reagents, methods, systems and kits for promoting bone growth at a site in a patient, and more specifically discloses utilizing a pump to supply a carrier matrix at the site with one or more therapeutic agents selected to promote bone growth.

One aspect of the invention provides a method for promoting bone growth at a target site in a patient. A carrier matrix is provided, which may be a suitable carrier matrix as known in the art.

This carrier matrix is implanted at the target site by way of a standard surgical procedure, as known in the art. A pump is then provided and primed with a suitable therapeutic agent that is adapted to promote bone growth. This therapeutic agent may comprise, for example, an active ingredient that was also originally present in the carrier matrix, or may provide a different active ingredient. An output port of the pump is fluidly connected with the carrier matrix so that the pump provides the therapeutic agent to the carrier matrix.

In one embodiment, the pump is disposed internally within the patient. In a specific variation, the output port of the pump is disposed within the carrier matrix, or contacts the carrier matrix. In another variation, the entire pump is disposed within the carrier matrix. In certain embodiments the pump is an osmotic pump.

In another embodiment any pump that can be miniaturized and adapted for internal dispensation of fluids in a patient may be used in the present invention. Suitable pumps include but not limited to, positive displacement pumps, kinetic pumps, electromagnetic pumps and gas lift pumps.

Positive displacement pumps that lift a given volume of fluid for each cycle of operation, can be divided into two main classes, reciprocating and rotary. Reciprocating pumps include piston, plunger, and diaphragm types; rotary pumps include gear, lobe, screw, vane, and cam pumps.

Kinetic pumps can be divided into two classes, centrifugal and regenerative. In kinetic pumps a velocity is imparted to the fluid. Most of this velocity head is then converted to a pressure head. Centrifugal pumps include radial, axial, and mixed flow units. A radial flow pump is commonly referred to as a straight centrifugal pump; the most common type is the volute pump. Another type of radial flow centrifugal pump is the diffuser pump, in which, after the fluid has left the impeller, it is passed through a ring of fixed vanes that diffuse the liquid, providing a more controlled flow and a more efficient conversion of velocity head into pressure head. A regenerative pump is also called a turbine, or peripheral, pump.

In one embodiment electromagnetic pumps generally used for pumping liquid metals could be used in the present invention.

Other types of pumps that could be used in the present invention include but not limited to Gas lift pumps. Gas lift pumps are used to raise liquids from the bottoms of fluid wells. In the jet ejector pump, fluid passes through a venturi nozzle and develops a suction that causes a second stream of fluid to be entrained. In the aspirator pump, fluid flows through a venturi nozzle and develops a suction for drawing in air. Steam ejectors are widely used for pumping large volumes of vapors and gases at low pressures. The hydraulic ram pump uses the energy of a downward-flowing stream of fluid to lift a proportion of the fluid to a higher level. Vacuum pumps are simply compressors that take in a gas at a pressure lower than atmospheric pressure, compress it, and discharge the gas at atmospheric pressure.

In another embodiment, a tube or other suitable fluid delivery device is used to fluidly connect the output port of the pump with the carrier matrix. The pump may disposed within the patient, or externally of the patient. The fluid delivery device may have one or several outlets to feed the therapeutic agent to the carrier matrix, and may have a single line or branching lines. Moreover, the pump may have several output ports, each with a respective fluid delivery device. Hence, the pump may be able to provide the therapeutic agent to one or several carrier matrices.

In a specific embodiment the pump is disposed externally of the patient and the fluid delivery device is a tube, such as a catheter, used to fluidly connect the pump with the carrier matrix. Under this configuration, the pump is initially primed to deliver a first therapeutic agent to the carrier matrix. After a first prescribed regimen, the pump is primed to deliver a second therapeutic agent to the carrier matrix for a second prescribed regimen.

In another embodiment, the carrier matrix is injectable. In this embodiment, the carrier matrix is first injected into the target site. Then, a catheter or like fluid delivery device is used to fluidly connect the implanted carrier matrix with the pump. The pump delivers the therapeutic agent to the carrier matrix in conformance with a prescribed treatment regiment to promote bone growth into the carrier matrix.

Another aspect of the invention provides a kit for promoting bone growth at a surgical site. The kit includes a carrier matrix adapted for implantation at a target site in a patient to support bone growth, and a pump adapted to deliver a therapeutic agent to the implanted carrier matrix.

DETAILED DESCRIPTION

Figure 1:
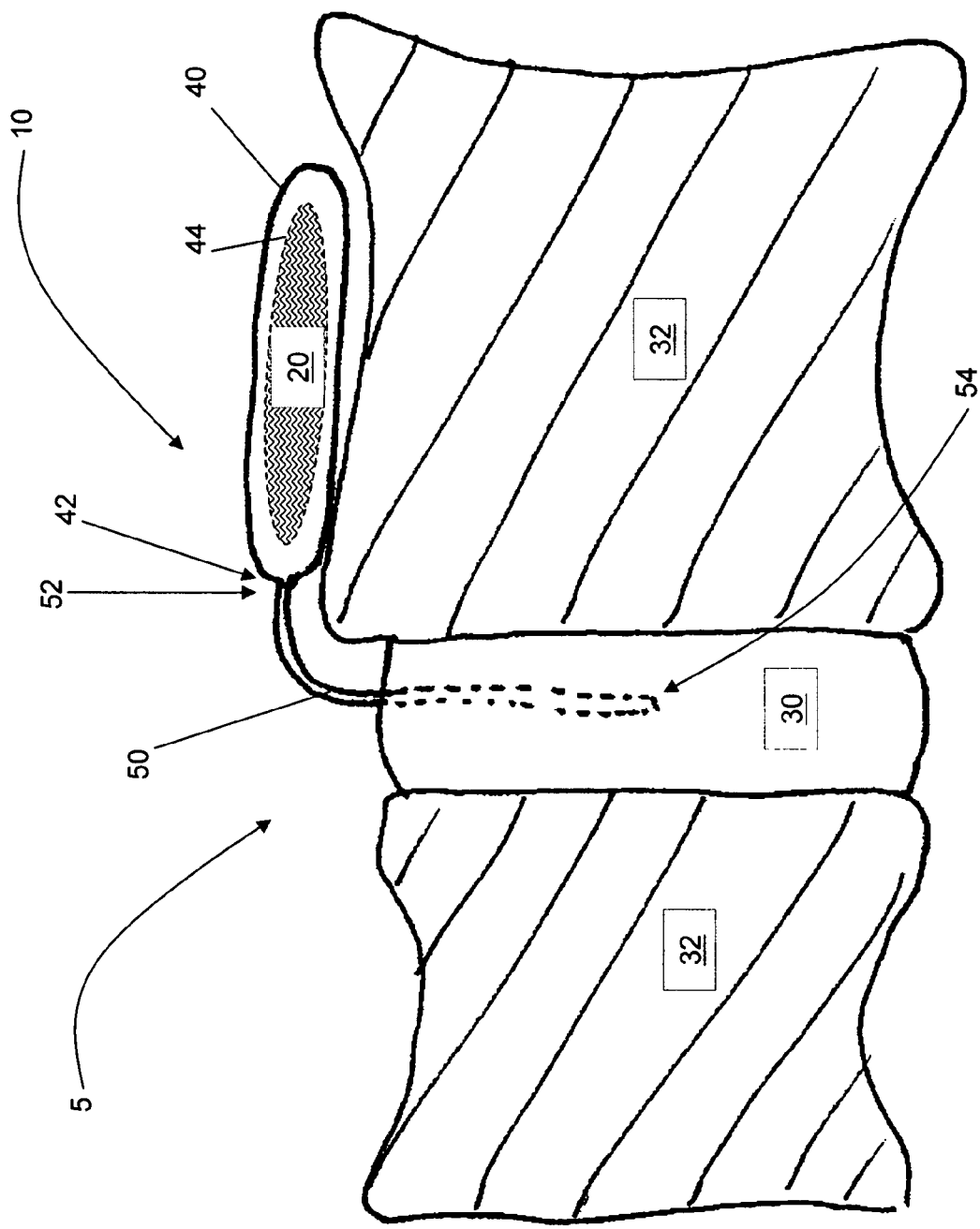
FIG. 1 shows a first embodiment according to the invention.

To aid in the understanding of the invention, the following non-limiting definitions are provided:

Used herein, a therapeutic agent is a medicinal composition designed to achieve a medically useful end. A therapeutic agent typically comprises at least one active ingredient, alone or with diluents, excipients and other pharmaceutically acceptable agents desirable for improved stability, manufacturing, efficacy and the like. As used herein, unless otherwise indicated, an active ingredient is a pharmacological substance known to promote bone growth, including cells that may be, but are not limited to, mesenchymal stem cells, osteoblasts, and osteoclasts. The active ingredient may promote bone growth through osteoinduction, osteoconduction and/or by facilitating osteogenic capabilities of the carrier matrix.

As indicated above, excipients may be employed in the therapeutic agent. The amount of excipient that is useful in the therapeutic agent is an amount that serves to uniformly distribute the one or more active ingredients throughout the therapeutic agent so that the active ingredient can be uniformly dispersed when delivered to a subject in need thereof. The excipient may serve to dilute the active ingredient to a concentration at which the desired beneficial palliative or curative results are obtained, while at the same time minimizing any adverse side effects that might occur from too high a concentration of active ingredient. The excipient may also have a preservative effect. Thus, for an active ingredient that has high physiological activity, more of the excipient will be employed. On the other hand, for an active ingredient that exhibits a lower physiological activity a lesser quantity of the excipient will be employed. In general, the amount of excipient in the composition will be between about 50% weight (w) and 99.9% w. of the total composition. For active ingredients that have particularly high physiological activities, the amount may be between about 98.0% and about 99.9% w. By way of example, rhBMP-2 can be used at a concentration of about 0.1 mg/ml to about 4.0 mg/ml, and preferably near 1.5 mg/ml.

"Localized" delivery is defined herein as non-systemic delivery in which a therapeutic agent is deposited within a tissue or carrier matrix, or in close proximity (within about 10 cm, or preferably within about 5 cm, for example) thereto. A "controlled administration system" provides localized delivery of one or more active ingredients in a quantity of therapeutic agent that can be deposited at the target site as needed, either continuously or at an intermittent rate. A "controlled administration system" includes, but is not limited to, an osmotic pump, an interbody pump, an infusion pump, implantable mini-pumps, a peristaltic pump, other pharmaceutical pumps, and an optional fluid delivery device. A fluid delivery device is any suitable device or material that can carry a fluid from one point to another, such as a catheter, tubing, wicking or the like, to fluidly connect the pump to the carrier matrix. It is understood that pumps can be internal or external as appropriate.

Potential drug delivery devices that may be suitable for adaptation to the present invention method include, but are not limited to, those devices found in U.S. Pat. No. 6,551,290 (Elsberry, et al.), which describes a medical catheter for targeted, specific drug delivery; U.S. Pat. No. 6,571,125 (Thompson), which describes an implantable medical device for controllably releasing a biologically-active agent; U.S. Pat. No. 6,594,880 (Elsberry), which describes an intraparenchymal infusion catheter system for delivering therapeutic agents to selected sites in an organism; and U.S. Pat. No. 5,752,930 (Rise, et al.), which describes an implantable catheter for infusing equal volumes of agents to spaced sites.

One example of a suitable pump is the SynchroMed® (Medtronic, Minneapolis, Minn.) pump. This pump has three sealed chambers. One contains an electronic module and battery. The second contains a peristaltic pump and drug reservoir. The third contains an inert gas, which provides the pressure needed to force the pharmaceutical composition into the peristaltic pump. To fill the pump, the therapeutic agent is injected through the reservoir fill port to the expandable reservoir. The inert gas creates pressure on the reservoir, and the pressure forces the therapeutic agent through a filter and into the pump chamber. The therapeutic agent is then pumped out of the device from the pump chamber and into the catheter, which will direct the therapeutic agent to the target site, i.e., within or near the carrier matrix. The rate of delivery of the therapeutic agent is controlled by a microprocessor. This allows the pump to be used to deliver similar or different amounts of the therapeutic agent continuously, at specific times, or at set intervals between deliveries, thereby controlling the release rates to correspond with the desired targeted release rates.

Additional designs which may be adapted to be employed in the method of the present invention are provided, for example, in United States patent applications, such as US 2002/0082583 (a pre-programmable implantable apparatus with a feedback regulated delivery method), US 2004/0106914 (a micro-reservoir osmotic release system for controlled release of chemicals), US 2004/0064088 (a small, light-weight device for delivering liquid medication), US 2004/0082908 (an implantable microminiature infusion device), US 2004/0098113 (an implantable ceramic valve pump assembly), and US 2004/0065615 (an implantable infusion pump with a collapsible fluid chamber). Alzet® osmotic pumps (Durect Corporation, Cupertino, Calif.) are also available in a variety of sizes, pumping rates and durations suitable for use in the method of the present invention. One of reasonable skill in the art will readily understand that other types or configurations of pumps and fluid delivery devices (i.e., catheters) may be adapted for use in the instant invention, and that the above are simply exemplary and by no means exhaustive.

The term "carrier matrix" refers to biomaterials for the orthopedic implant market which, when placed in a bone defect, provide scaffolding through and around which the patient's new bone will grow, gradually replacing the carrier matrix as the target site heals. Examples of suitable carrier matrices may include, but are not limited to, the MasterGraft® Matrix produced by Medtronic Sofamor Danek, Inc., Memphis, Tenn.; MasterGraft® Putty produced by Medtronic Sofamor Danek, Inc., Memphis, Tenn.; Absorbable Collagen Sponge ("ACS") produced by Integra LifeSciences Corporation, Plainsboro, N.J.; Collagraft® Bone Graft Matrix produced by Zimmer Holdings, Inc., Warsaw, Ind.; tricalcium phosphate granules e.g. ChronOS® or Ceros® TCP produced by Mathys Ltd., Switzerland; Norian injectable cements marketed by Norian/Synthes, USA; porous bone graft substitute, e.g. ProOsteon Implant 500® marketed by Interpore Int., USA; micro glass granules e.g. BiGran® marketed by Orthovita, USA; calcium phosphate e.g. Alpha BSM®, marketed by ETEX Corp., USA; calcium phosphate-based bone cement e.g. BoneSource®, marketed by Orthofix Inc., USA; gel, putty and flex forms, e.g. Grafton DMB®, marketed by Osteotech Inc., USA; artificial formable bone matrix marketed by Bioapatite AB, Sweden; bovine skin collagen fibers coated with hydroxyapatite, e.g. Healos® marketed by Johnson & Johnson, USA; collagen sponges, e.g. Hemostagene® marketed by Coletica SA, France, or e.g. Helisat® marketed by Integra Life Sciences Inc., USA; bioresorbable polymer and bone cement, e.g. OrthoDyn marketed by DynaGen Inc., USA; biodegradable POB/PBT copolymers marketed by IsoTis B. V., Netherlands; biodegradable polymers, e.g. Prolease® and Medisorb® marketed by Alkermes, USA; bone chips (e.g. 30/70 cortical/cancellous); calcium aluminates; and hydrogels. The carrier matrix may also be injectable; examples of such injectable matrices include Norian® SRS® Bone Void Filler, Synthes, West Chester, Pa.; CORTOSS® Injectable Synthetic Bone Filler, Orthovita, Malvern, Pa.; and Cerament Bone Void Filler, Bone Support AB, Sweden. Other materials that are suitable as matrices include polysaccharides, proteins and polypeptides, glycosaminoglycans, proteoglycans, collagen, elastin, hyaluronic acid, dermatan sulfate, chitin, chitosan, pectin, (modified) dextran, (modified) starch, or mixtures or composites thereof. Synthetic polymers may also be employed, including for example biodegradable synthetic polymers such as polylactic acid, polyglycolide, polylactic polyglycolic acid copolymers ("PLGA"), polycaprolactone ("PCL"), poly(dioxanone), poly(trimethylene carbonate) copolymers, polyglyconate, poly(propylene fumarate), poly(ethylene terephthalate), poly(butylene terephthalate), polyethyleneglycol, polycaprolactone copolymers, polyhydroxybutyrate, polyhydroxyvalerate, tyrosine-derived polycarbonates and any random or (multi-)block copolymers, such as bipolymer, terpolymer, quaterpolymer, etc., that can be polymerized from the monomers related to the previously-listed homo- and copolymers. Also, a mineral component can be used as a carrier. The mineral used can include a natural or synthetic mineral that is effective to provide a scaffold for bone ingrowth. For example, the mineral matrix may be selected from one or more materials from the group consisting of bone particles, Bioglass®, tricalcium phosphate, biphasic calcium phosphate, hydroxyapatite, corraline hydroxyapatite, and biocompatible ceramics. Biphasic calcium phosphate may be a particularly desirable synthetic ceramic for use as a carrier matrix.

The term "osteoinduction" refers to the ability to stimulate the proliferation and differentiation of pluripotent mesenchymal stem cells (MSCs). In endochondral bone formation, stem cells differentiate into chondroblasts and chondrocytes, laying down a cartilaginous ECM, which subsequently calcifies and is remodeled into lamellar bone. In intramembranous bone formation, the stem cells differentiate directly into osteoblasts, which form bone through direct mechanisms. Osteoinduction can be stimulated by osteogenic growth factors, although some ECM proteins can also drive progenitor cells toward the osteogenic phenotype.

The term "osteogenic" refers to the ability of a carrier matrix material to produce bone. To have direct osteogenic activity, the carrier matrix must contain osteogenic factors, such as cellular components that directly induce bone formation. For example, a collagen matrix seeded with activated MSCs would have the potential to induce bone formation directly, without recruitment and activation of host MSC populations. Because many osteoconductive scaffolds also have the ability to bind and deliver bioactive molecules, their osteoinductive potential may be greatly enhanced. Suitable osteogenic factors include mesenchymal stem cells, blood or blood fractions, bone marrow or bone marrow fractions, and/or other sources of cells or other beneficial tissue components derived from the patient to be treated or another suitable animal source. In certain embodiments, a therapeutic agent may comprise one or more osteogenic factors as an active ingredient.

The term "osteoconduction" refers to the ability to stimulate the attachment, migration, and distribution of vascular and osteogenic cells within the carrier matrix material. The physical characteristics that affect the osteoconductive activity of the carrier matrix include porosity, pore size, and the three-dimensional architecture of the matrix. In addition, direct biochemical interactions between matrix proteins and cell surface receptors play a major role in the host's response to the carrier matrix material.

Depending upon the condition of the patient, new bone ingrowth is accomplished by one or more mechanisms, such as osteogenesis, osteoconduction and osteoinduction. It can be appreciated that the needs of a child are different from an aging patient afflicted with osteoporosis. Accordingly, there is no "one size fits all" approach towards optimizing the healing conditions in a patient, and treatment regimens must be tailored accordingly. Developing a regimen suited to the needs of a patient is an ordinary skill in the art, which may be provided by a suitable practitioner, such as a doctor. The present invention particularly contemplates treatment regimens that are adapted for patients that are suffering slow growth of the bone tissue. This may occur in certain types of fractures, such as closed fractures, or in patients suffering diabetes, who are smokers, or who are using steroids.

The preferred active ingredients are morphogens. The term "morphogen" refers to an osteoinductive factor that stimulates or induces bone growth. Example morphogens include, but are not limited to, Bone Morphogenetic Proteins (BMPs), including BMP-1, BMP-2, BMP-3, BMP-4, BMP-5, BMP-6, BMP-7, BMP-8, BMP-9, BMP-10, BMP-11, BMP-12, BMP-13, BMP-14, BMP-15, BMP-16, BMP-17, and BMP-18; Vascular Endothelial Growth Factors (VEGFs), including VEGF-A, VEGF-B, VEGF-C, VEGF-D and VEGF-E; Connective Tissue Growth Factors (CTGFs), including CTGF-1, CTGF-2, and CTGF-3; Osteoprotegerin, Transforming Growth Factor betas (TGF-βs), including TGF-β-1, TGF-β-2, and TGF-β-3, and inhibitors for tumor necrosis factor (e.g., Enbrel®). Morphogens may also include Platelet Derived Growth Factors (PDGFs), including PDGF-A, PDGF-B, PDGF-C, PDGF-D, and GDF-5; rhGDF-5; and LIM mineralization protein, insulin-related growth factor-I (IGF-I), insulin-related growth factor-II (IGF-II), fibroblast growth factor (FGF) and beta-2-microglobulin (BDGF II), as disclosed in the U.S. Pat. No. 6,630,153, which is incorporated herein by reference. The polynucleotides encoding the same may also be administered as gene therapy agents. The preferred morphogens are the recombinant human bone morphogenetic proteins (rhBMPs) because they are available in relatively unlimited supply and do not transmit infectious diseases. Most preferably, the bone morphogenetic protein is a rhBMP-2, rhBMP-4, rhBMP-7, or heterodimers thereof. BMP-7 is available form Stryker Corp., USA and other BMPs are available from Wyeth, Madison, N.J., and may also be prepared by one skilled in the art as described in U.S. Pat. No. 5,366,875 to Wozney et al.; U.S. Pat. No. 4,877,864 to Wang et al.; U.S. Pat. No. 5,108,922 to Wang et al.; U.S. Pat. No. 5,116,738 to Wang et al.; U.S. Pat. No. 5,013,649 to Wang et al.; U.S. Pat. No. 5,106,748 to Wozney et al.; and PCT Patent Nos. WO93/00432 to Wozney et al.; WO94/26893 to Celeste et al.; and WO94/26892 to Celeste et al.

The term "treating" or "treatment" of a disease refers to executing a treatment regimen, which may include administering one or more therapeutic agents to a patient (human or otherwise), in an effort to alleviate signs or symptoms of the disease. Alleviation can occur prior to signs or symptoms of the disease appearing, as well as after their appearance. Thus, "treating" or "treatment" includes "preventing" or "prevention" of disease. In addition, "treating" or "treatment" does not require complete alleviation of signs or symptoms, does not require a cure, and specifically includes regimens which have only a marginal effect on the patient.

The term "patient" refers to a biological system to which a treatment can be administered. A biological system can include, for example, an individual cell, a set of cells (e.g., a cell culture), an organ, a tissue, or a multi-cellular organism. A patient can refer to a human patient or a non-human patient.

By "comprising" is meant including, but not limited to, whatever follows the word "comprising". Thus, use of the term "comprising" indicates that the listed elements are required or mandatory, but that other elements are optional and may or may not be present. Additionally, unless otherwise noted, exemplary lists of compounds or devices should not be construed as limiting; instead, it should be understood that such lists admit to additional, suitable items not explicitly indicated.

A kit of the present invention may comprise a carrier matrix and a pump adapted to provide a therapeutic agent to the carrier matrix. As described above, the carrier matrix is designed to support bone growth. The therapeutic agent should comprise one or more active ingredients, as discussed above, that promote bone growth. The kit may optionally include the therapeutic agent. The kit may also optionally include one or more tubes, catheters, micro-catheters, wicks or the like to serve as fluid delivery devices that carry the therapeutic agent from the pump to the carrier matrix within the patient. The kit may include a sterilized container or packaging, as known in the art, to preserve the integrity and cleanliness of the various components of the kit. The following various embodiments illustrate exemplary kits of the present invention being utilized in a patient according to the invention method.

By way of example only, in one embodiment, as shown in FIG. 1, a controlled administration system 10 provides localized delivery of an effective amount of a therapeutic agent 20 to a carrier matrix 30. The carrier matrix 30 is disposed in a target site 5, typically adjacent to one or more bone structures 32, and could be, for example, the INFUSE® Bone Graft product (Medtronic Sofamor Danek, Memphis, Tenn.) for use as an autograft replacement in a lumbar spinal fusion procedure. The INFUSE® product is an rhBMP-2/ACS combination implant, which may also be used for acute tibial fractures. To use INFUSE® Bone Graft, a surgeon reconstitutes rhBMP-2 powder with sterile water and then applies the resultant solution to the ACS. The sponges are inserted inside medical devices, such as an LT-Cage, INTER FIX and/or INTER FIX RP Threaded Fusion Devices, a pair of which is then implanted between the vertebrae 32.

The controlled administration system 10 delivers the therapeutic agent 20 to the carrier matrix 30 according to a treatment regimen as provided by a doctor; as previously indicated, the therapeutic agent 20 is designed to promote bone growth into the carrier matrix 30. The controlled administration system 10 comprises a pump 40 fluidly connected to a tube 50, which may be a micro-catheter. The pump 40 is disposed internally within the patient, and may be implanted when the carrier matrix 30 is implanted. The pump 40 comprises a reservoir 44 of the therapeutic agent 20, and has an outlet port 42 from which the therapeutic agent 20 is dispensed. The reservoir 44 shields the active ingredient(s) within the therapeutic agent 20 from substances in and near the target site 5 that might otherwise cause degradation of the active ingredient(s). A proximal end 52 of the tube 50 is fluidly connected to the outlet port 42. A distal end 54 of the tube 50 is in fluid communications with the carrier matrix 30. In the embodiment depicted in FIG. 1, the distal end 54 is disposed within the carrier matrix 30. The therapeutic agent 20 thus exits the distal end 54 of the tube 50 and then diffuses outward from a central region within the carrier matrix 30. Of course, the distal end 54 may be placed in other locations; for example, the distal end 54 may be located on the outer surface of the carrier matrix 30. Regardless of the physical placement of the distal end 54, or indeed of the entire controlled administration system 10, the end result should be that the therapeutic agent 20 contained within the reservoir 44 is finally delivered to the carrier matrix 30. The specific placement details of the controlled administration system 10 may be determined by one of reasonable skill in the art.

Figure 2:
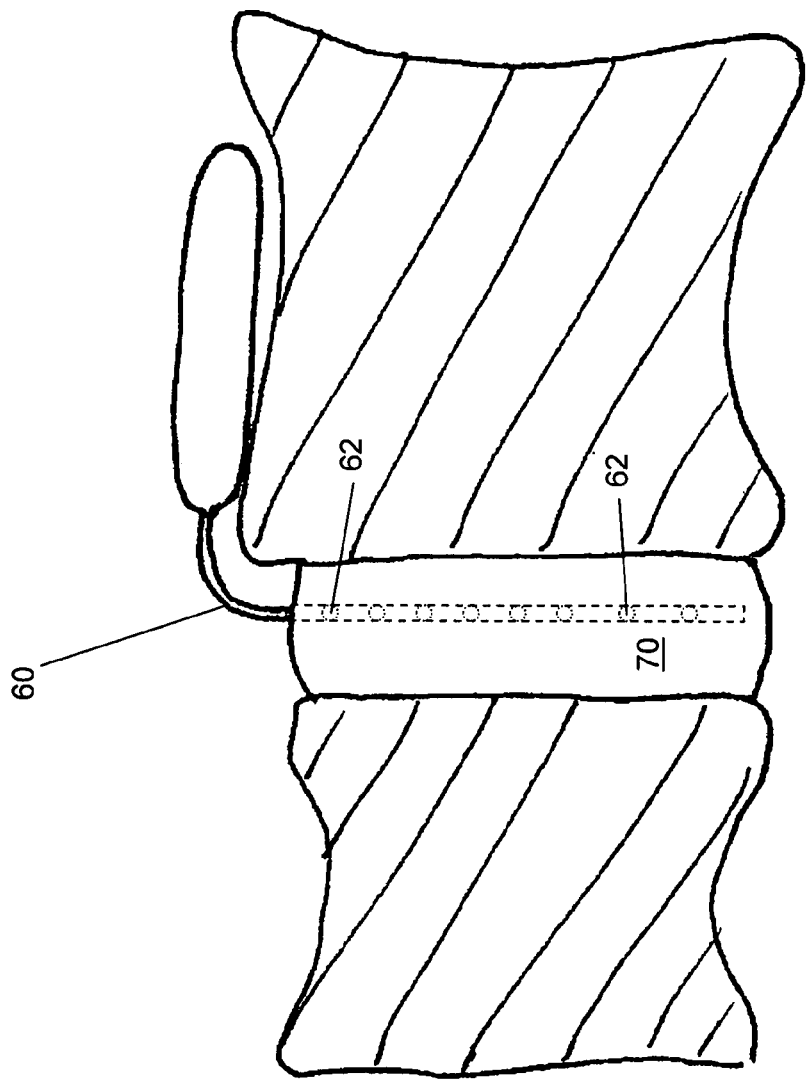
FIG. 2 shows a second embodiment of the invention.

An alternate embodiment is shown in FIG. 2, which is substantially the same as that shown in FIG. 1 except that a catheter 60 comprises a plurality of outlets 62 from which the therapeutic agent may leach into the carrier matrix 70. The outlets 62 may have different sizes so that each outlet 62 delivers about the therapeutic agent at about the same rate.

Figure 3:
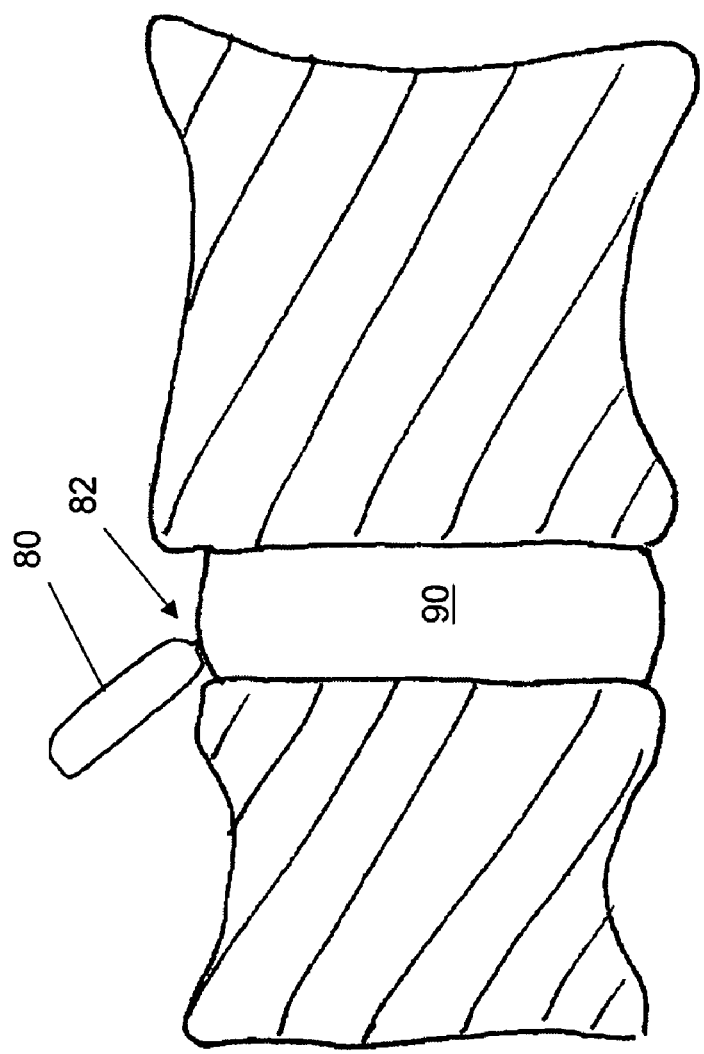
FIG. 3 shows a third embodiment of the invention.
Figure 4:
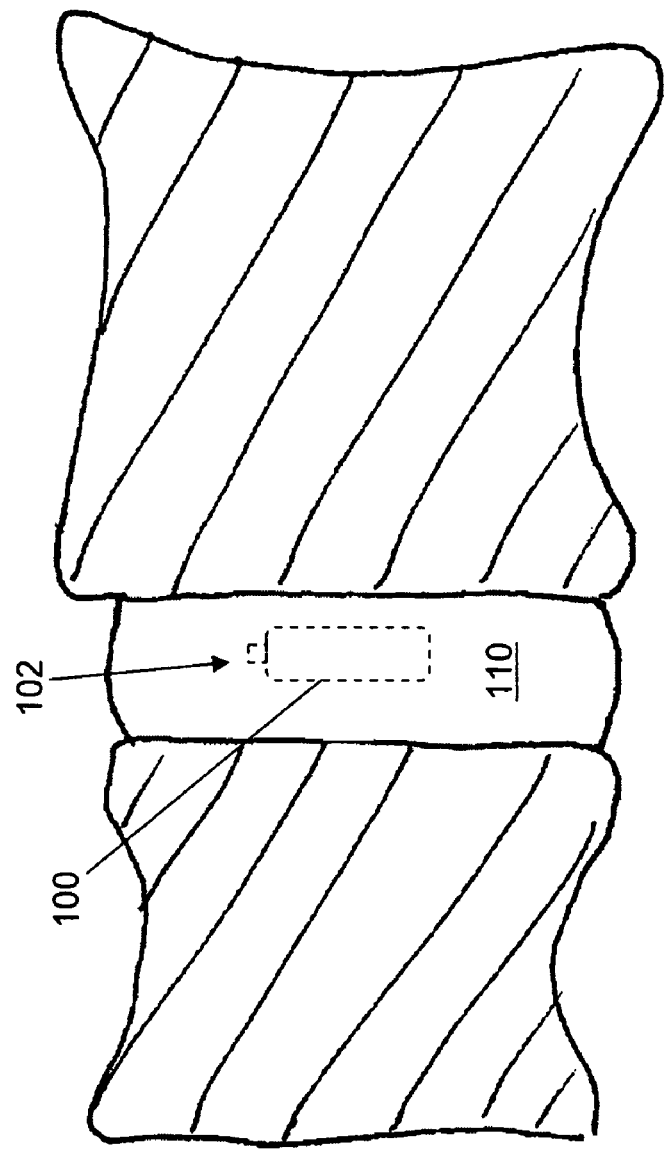
FIG. 4 shows a fourth embodiment of the invention.

As shown in FIGS. 3 and 4, when the pump is disposed internally within the patient, a catheter is not necessarily required. For example, as shown in FIG. 3, a pump 80 with an outlet port 82 may be implanted into tissue directly adjacent to the carrier matrix 90. The pump 80 is positioned so that the outlet 82 is disposed in, close to or touching the carrier matrix 90 The outlet port 82 should be within at least 5 cm of the carrier matrix 90, more preferably within 5 mm of the carrier matrix 90, and even more preferably touching or disposed within the carrier matrix 90. As shown in FIG. 4, a pump 100 may be entirely disposed within carrier matrix 110. In this embodiment, the pump 100 may have more than one outlet port 102.

Figure 5:
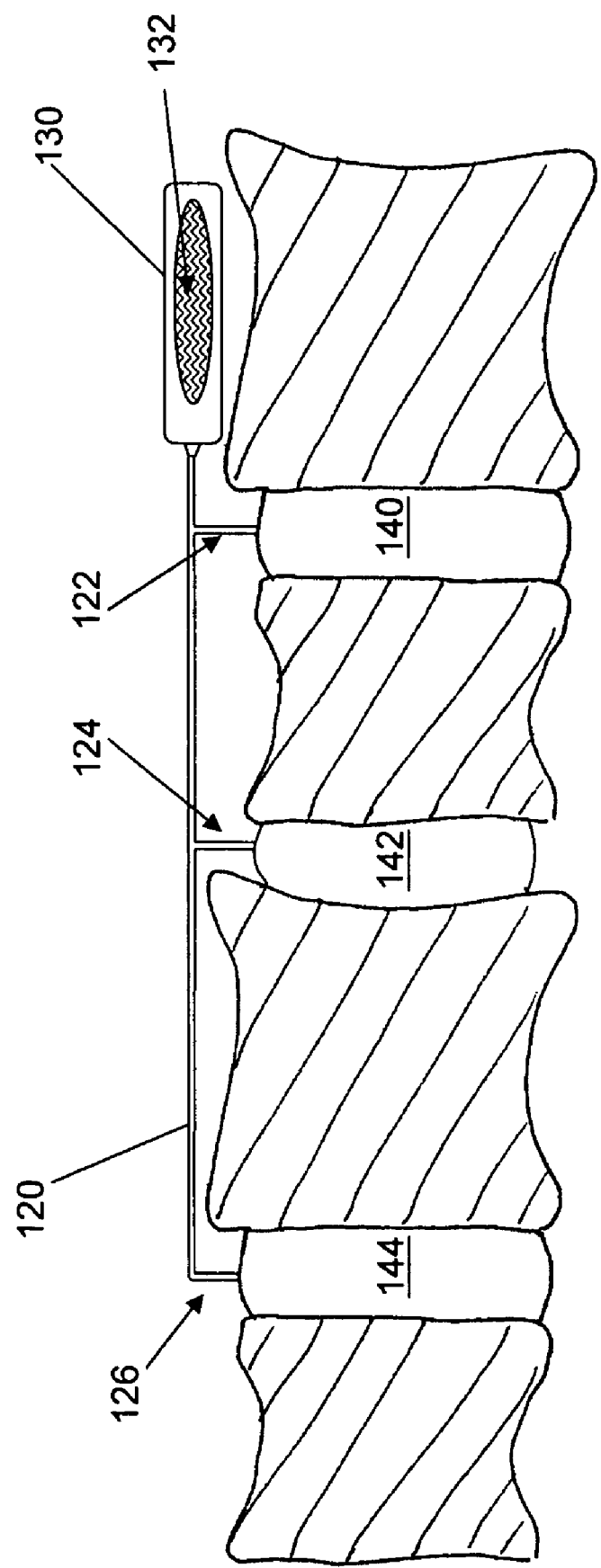
FIG. 5 shows a fifth embodiment of the invention.
Figure 6:
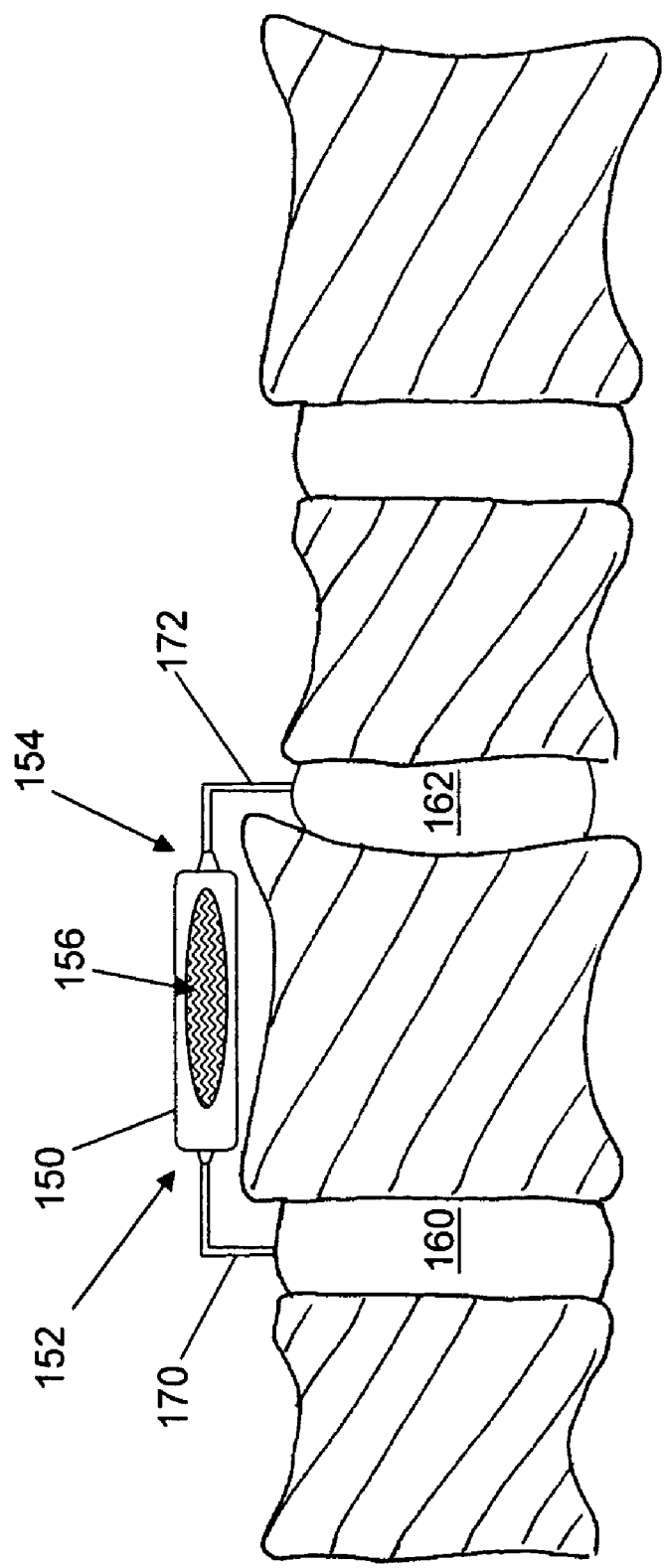
FIG. 6 shows a sixth embodiment of the invention.

As shown in FIGS. 5 and 6, a single pump may provide a therapeutic agent to more than just one carrier matrix. For example, with respect to FIG. 5, a tube 120, fluidly connected to a pump 130, may have several branches 122, 124, 126. Each branch 122, 124, 126 may deliver the therapeutic agent 132 to a respective carrier matrix 140, 142, 144. Alternative, as shown in FIG. 6, a single pump 150 may have two or more output ports 152, 154. Each output port 152, 154 may have a respective tube 170, 172, which respectively feeds therapeutic agent 156 to carrier matrices 160, 162.

Figure 7:
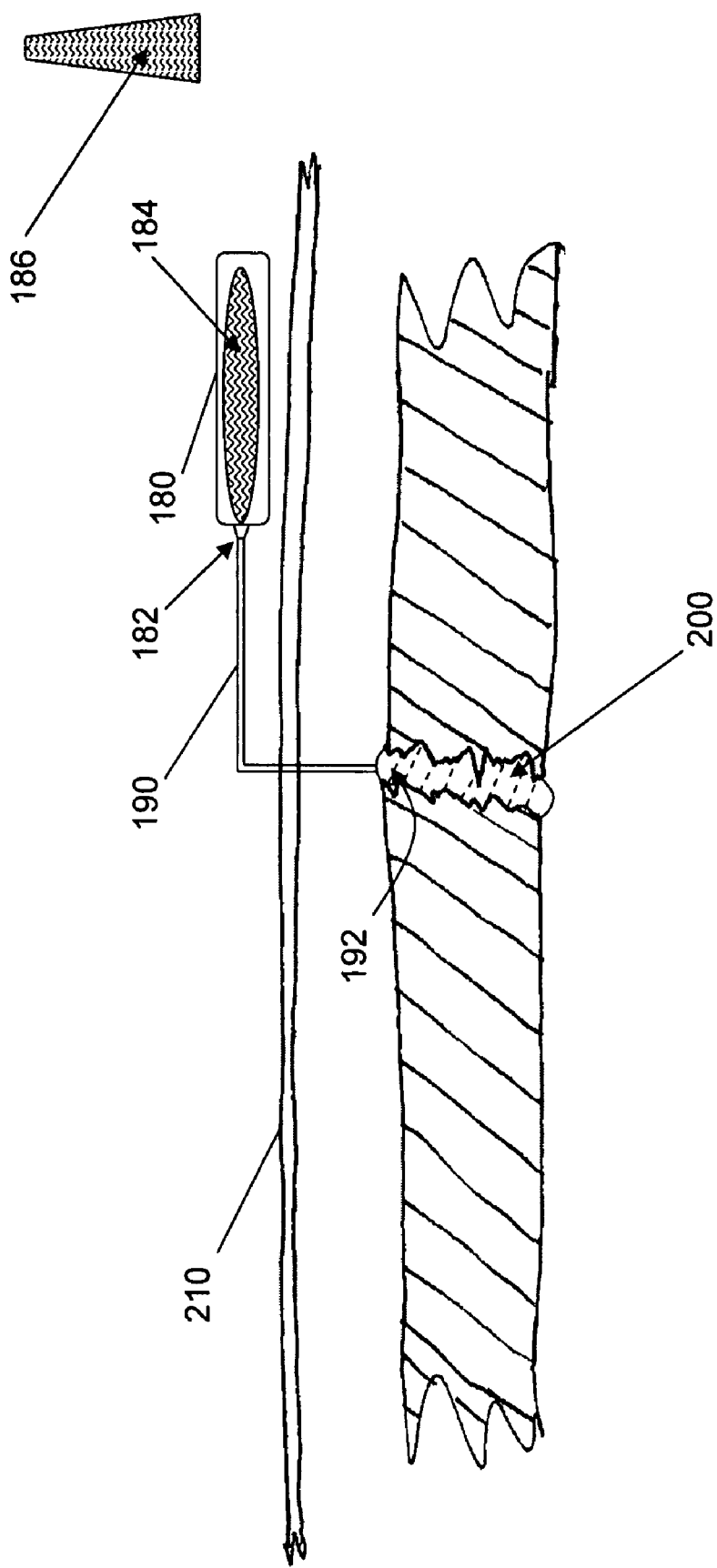
FIG. 7 shows a seventh embodiment of the invention.

Of course, the pump need not always be disposed within the patient. As shown in FIG. 7, it is possible to provide for an external pump 180 that, via a catheter 190 fluidly connected to the output port 182 of the pump 180, delivers a first therapeutic agent 184 to a carrier matrix 200. The catheter 190 passes through a skin layer 210 so that a distal end 192 of the catheter 190 can provide the first therapeutic agent 184 to the carrier matrix 190. One benefit of this arrangement is that for extended therapies the pump 184 may be conveniently reloaded with the first therapeutic agent 184. Alternatively, after the regimen for the first therapeutic agent 184 has been completed, the pump 180 may be loaded with a second therapeutic agent 186. Thereafter, the pump 180 will deliver the second therapeutic agent 186 to the carrier matrix 190 for a second treatment regimen. Another benefit of utilizing the external pump 180 is that either of the therapeutic agents 184, 186 may comprise cells as an active ingredient to promote bone growth.

Figure 8:
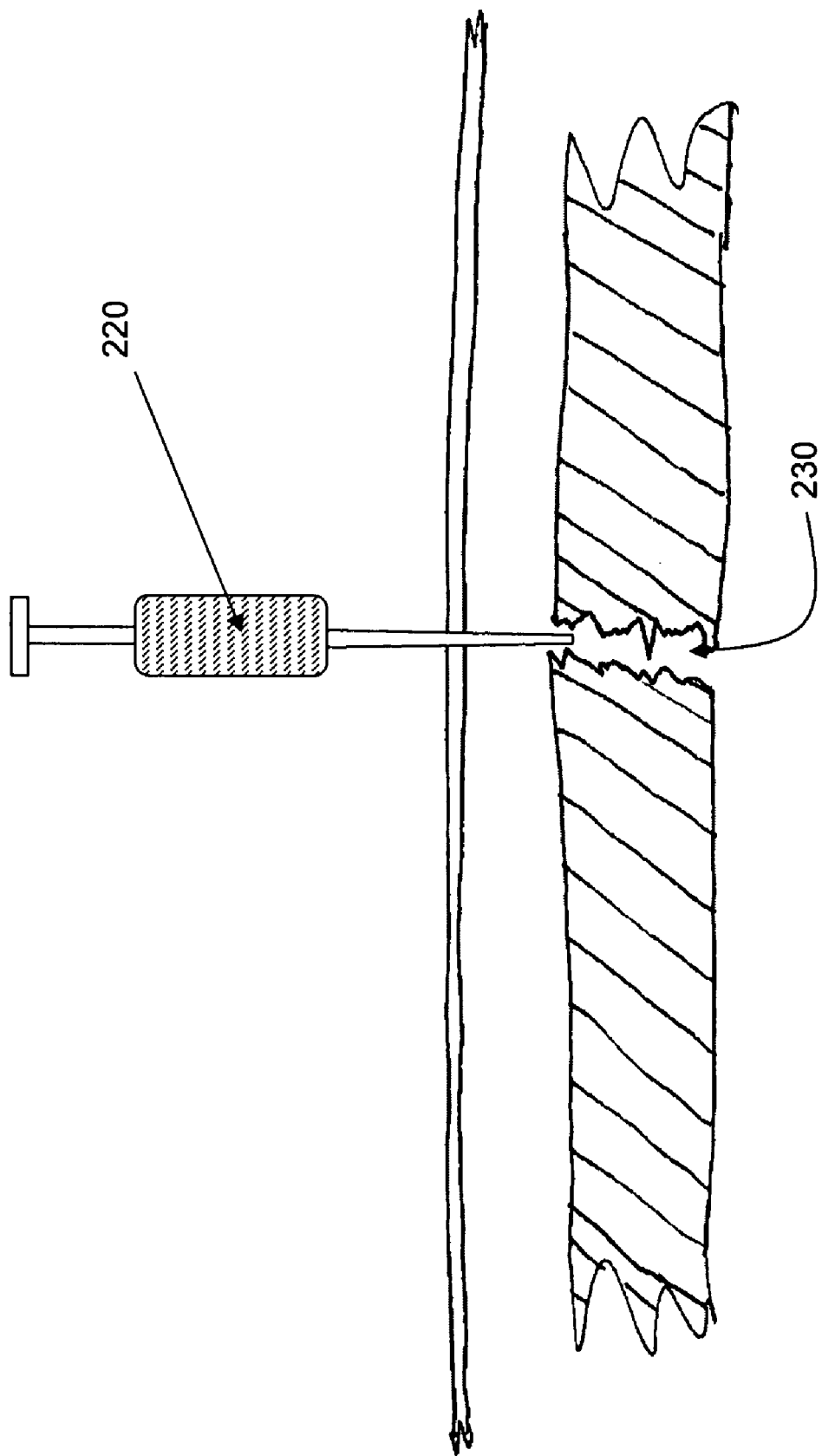
FIG. 8 illustrates injection of a carrier matrix according to one aspect of the invention.

As shown in FIG. 8, the carrier matrix 220 may be in the form of an injectable gel or the like. The carrier matrix 220 is injected into the target site 230. When the target site 230 has been sufficiently filled with the carrier matrix 220, then as previously indicated in FIG. 7, a distal end of a catheter may be fed into the carrier matrix 220 within the target site 230, and the proximal end of the catheter may be connected to a pump to deliver a therapeutic agent to the carrier matrix 220 according to a treatment regimen.

All publications cited in the specification, both patent publications and non-patent publications, are indicative of the level of skill of those skilled in the art to which this invention pertains. All these publications are herein fully incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

What is claimed is:

1. A method for promoting bone growth in a patient, the method comprising: disposing a carrier matrix at a target site in the patient, the carrier matrix comprising a collagen sponge and a pump capable of delivering an effective amount of a first therapeutic agent, the first therapeutic agent adapted to promote bone growth and comprising bone morphogenetic protein 2; and fluidly connecting the pump within the carrier matrix so as to deliver 0.1 mg/ml to 4.0 mg/ml of bone morphogenetic protein 2 to the carrier matrix.

2. The method of claim 1, wherein the pump does not contain a catheter.

3. The method of claim 1, wherein the pump is an osmotic pump.

4. The method of claim 1 wherein the therapeutic agent further comprises a drug, a cellular matter, or a combination thereof.

5. The method of claim 1, wherein the first therapeutic agent further comprises a cartilage-derived morphogenetic protein (CDMP), a platelet derived growth factor (PDGF), an insulin-like growth factor (IGF), LIM mineralization protein, a fibroblast growth factor (FGF), osteoblast growth factor, a Transforming Growth Factor (TGF) beta or a combination thereof.

6. The method of claim 1 further comprising: loading the pump with a second therapeutic agent; and causing the pump to deliver the second therapeutic agent to the carrier matrix.

7. The method of claim 6 wherein the second therapeutic agent is adapted to promote anti-inflammatory activity.

8. The method of claim 6 wherein the first therapeutic agent further comprises an active ingredient selected from the group consisting of a drug, a cellular matter, and a combination thereof.

9. The method of claim 6, wherein the first therapeutic agent further comprises a cartilage-derived morphogenetic protein (CDMP), a platelet derived growth factor (PDGF), an insulin-like growth factor (IGF), LIM mineralization protein, a fibroblast growth factor (FGF), osteoblast growth factor, a Transforming Growth Factor (TGF) beta or a combination thereof.

10. A method for promoting bone growth in a patient, the method comprising: disposing a carrier matrix at a target site in the patient, the carrier matrix comprising a collagen sponge and a pump disposed entirely within the carrier matrix, the pump capable of delivering an effective amount of a first therapeutic agent, the first therapeutic agent adapted to promote bone growth and comprising bone morphogenetic protein 2; and the pump being fluidly connected to the carrier matrix so as to deliver 0.1 mg/ml to 4.0 mg/ml of the bone morphogenetic protein 2 to the carrier matrix.

11. The method of claim 10 wherein the first therapeutic agent further comprises an active ingredient selected from the group consisting of a drug, a cellular matter, and a combination thereof.

12. The method of claim 1 wherein the carrier matrix further comprises bone chips, a calcium phosphate ceramic, a collagen/mineral combination, calcium aluminates, or a hydrogel.

13. The method of claim 1 wherein the treatment regimen is adapted for a slow-healing fracture and the carrier matrix does not contain a catheter.

14. A kit for promoting bone growth at a site in a patient comprising: a carrier matrix adapted for implantation at a target site in a patient to support bone growth, the carrier matrix comprising a collagen sponge; and
    a pump disposed within the carrier matrix adapted to deliver 0.1 mg/ml to 4.0 mg/ml of the bone morphogenetic protein 2 to the carrier matrix, when the carrier matrix is implanted; and a set of instructions.

15. The kit of claim 14, wherein the set of instructions comprises instructions on how to administer the carrier matrix to the patient.

* * * * *